US012265877B2

(12) United States Patent
Mongrenier

(10) Patent No.: US 12,265,877 B2
(45) Date of Patent: Apr. 1, 2025

(54) DISPENSER FOR CONTROLLING A MEDICAL PRODUCT CONTAINER, AND ASSOCIATED ASSEMBLY, FACILITY AND CONTROL METHOD

(71) Applicant: BIOLOG-ID, Boulogne-Billancourt (FR)

(72) Inventor: Jean-Claude Mongrenier, Versailles (FR)

(73) Assignee: BIOLOG-ID, Boulogne-Billancourt (FR)

( * ) Notice: Subject to any disclaimer, the term of this patent is extended or adjusted under 35 U.S.C. 154(b) by 920 days.

(21) Appl. No.: 17/284,391

(22) PCT Filed: Nov. 23, 2018

(86) PCT No.: PCT/EP2018/082447
§ 371 (c)(1),
(2) Date: Apr. 9, 2021

(87) PCT Pub. No.: WO2020/074110
PCT Pub. Date: Apr. 16, 2020

(65) Prior Publication Data
US 2021/0342558 A1    Nov. 4, 2021

(30) Foreign Application Priority Data
Oct. 12, 2018   (FR) ................................ 18 59491

(51) Int. Cl.
*G16H 40/67*    (2018.01)
*G06K 7/10*    (2006.01)
(Continued)

(52) U.S. Cl.
CPC ..... *G06K 7/10356* (2013.01); *G06K 19/0723* (2013.01); *G16H 20/10* (2018.01);
(Continued)

(58) Field of Classification Search
CPC .......... G06K 7/10356; G06K 19/0723; G16H 20/10; G16H 40/20; G16H 40/67; G16H 40/63; A61J 2205/60
See application file for complete search history.

(56) References Cited

U.S. PATENT DOCUMENTS

| 6,703,935 B1 * | 3/2004 | Chung ............... G08B 13/2477 343/866 |
| 7,158,030 B2 * | 1/2007 | Chung .................... H01Q 7/00 340/5.1 |

(Continued)

FOREIGN PATENT DOCUMENTS

WO    2018/083399    5/2018

OTHER PUBLICATIONS

International Search Report for PCT/EP2018/082447 dated May 7, 2019, 5 pages.
(Continued)

*Primary Examiner* — Patrick H Mackey
(74) *Attorney, Agent, or Firm* — NIXON & VANDERHYE

(57) ABSTRACT

Disclosed is a dispenser for controlling at least one container including a medical product, the at least one container being provided with an electronic tag, the dispenser including: a plurality of inner walls delimiting a storage volume, the plurality of inner walls including side walls delimiting a single access opening for the storage volume, the dispenser being suitable for receiving at least one container; and a reader capable of reading the at least one information item stored in the memory of each electronic tag, the reader including a plurality of loop-shaped antennas, each side wall including a support able to house at least one part of one of the antennas.

19 Claims, 16 Drawing Sheets

(51) Int. Cl.
  *G06K 19/07* (2006.01)
  *G16H 20/10* (2018.01)
  *G16H 40/20* (2018.01)
  *A61J 1/05* (2006.01)
  *G16H 10/65* (2018.01)

(52) U.S. Cl.
  CPC ............ G16H 40/20 (2018.01); G16H 40/67 (2018.01); *A61J 1/05* (2013.01); *A61J 2205/60* (2013.01); *G16H 10/65* (2018.01)

(56) References Cited

U.S. PATENT DOCUMENTS

| | | | | |
|---|---|---|---|---|
| 7,432,874 | B2* | 10/2008 | Meissner | G06K 7/10356 |
| | | | | 343/742 |
| 7,648,065 | B2* | 1/2010 | Marino | H01Q 1/44 |
| | | | | 235/383 |
| 7,672,872 | B2 | 3/2010 | Shanton | |
| 9,959,387 | B2* | 5/2018 | Liguori | G16H 40/20 |
| 2005/0040934 | A1* | 2/2005 | Shanton | H04L 67/04 |
| | | | | 340/5.92 |
| 2010/0182149 | A1* | 7/2010 | Marino | G06K 7/10356 |
| | | | | 340/572.7 |
| 2022/0151421 | A1* | 5/2022 | Sengstaken, Jr. | G06K 7/10009 |

OTHER PUBLICATIONS

Written Opinion of the ISA for PCT/EP2018/082447 dated May 7, 2019, 7 pages.
French Search Report for FR 18 59491 dated Jun. 24, 2019, 2 pages.

* cited by examiner

FIG.15

DISPENSER FOR CONTROLLING A MEDICAL PRODUCT CONTAINER, AND ASSOCIATED ASSEMBLY, FACILITY AND CONTROL METHOD

CROSS-REFERENCE TO RELATED APPLICATIONS

This application is the U.S. national phase of International Application No. PCT/EP2018/082447 filed Nov. 23, 2018 which designated the U.S. and claims priority to FR 18 59491 filed Oct. 12, 2018, the entire contents of each of which are hereby incorporated by reference.

TECHNICAL FIELD OF THE INVENTION

The present invention concerns a dispenser. The invention also relates to a facility and a control system comprising such a dispenser and an associated control method.

TECHNOLOGICAL BACKGROUND

The present invention relates to the medical field, more specifically to the area of chemotherapy.

Chemotherapy is the use of certain chemical substances to treat a disease. It is a treatment technique in its own right in the same way as surgery or radiotherapy.

The term "chemotherapy" is mainly used to refer to drug treatments (cytostatic and antineoplastic chemotherapeutic agents) against cancer. Antibiotic therapy is referred to as antibacterial chemotherapy, but in medical practice the word is more commonly used in the context of tuberculosis treatment.

Another use of chemotherapeutic agents is in the treatment of autoimmune diseases.

As with any treatment, chemotherapy is very much dependent on the individual patient. The administration of a chemotherapy preparation intended for one patient to another can therefore have serious consequences for the patient's health.

However, in hospitals, errors are observed, and these errors are detrimental not only to the patient's health, but also to the reputation of the hospital.

SUMMARY OF THE INVENTION

Therefore, there is a need for a device that enables, with easy implementation, an increase in the ability to control the products administered to a patient with greater reliability.

To this end, the present description concerns a dispenser for the control of at least one container comprising a medical product, at least one container being provided with an electronic tag comprising a memory storing at least one information item specific to said medical product, the dispenser comprising multiple inner walls delimiting a storage volume, the multiple inner walls comprising side walls and a bottom wall on which the containers or the package comprising the containers are intended to rest, the side walls delimiting a single access opening to the storage volume, the dispenser being able to receive at least one container or a package comprising at least one container in the storage volume; and a reader able to read at least one information item stored in the memory of each electronic label, the reader comprising multiple loop-shaped antennas, each side wall comprising a support able to house at least part of one of the antennas.

According to a particular embodiment, the dispenser has one or more of the following features, taken separately or in any technically possible combination:
  the reader includes at least four side antennas, each side wall receiving at least one side antenna.
  each antenna defines an inner surface, the ratio between the inner surface of each side antenna and the surface of the associated side wall being greater than or equal to 75%.
  the access opening defines an opening plane, at least one antenna being arranged on all the side walls and extending in the opening plane, and at least one antenna being arranged on all the side walls away from the opening plane.
  the inner walls are made of plastic.
  each antenna is a coaxial cable.
  the reader further comprises at least one reading module configured to read at least one information item stored in the memory of each electronic tag and to send a signal comprising at least one information to a controller external to the dispenser; and a multiplexer connecting the antennas to the reading module.
  the reader is able to transmit or receive a signal a signal having a frequency between 13.540 MHz and 13.567 MHz.
  the multiple walls comprise outer walls, each outer wall being made of an electrically conductive material having an electrical conductivity greater than or equal to $0.3 \text{ MS.cm}^{-1}$, the outer walls delimiting an inner volume, the storage volume being disposed in the inner volume.
  the dispenser has a volume of less than $0.1 \text{ m}^3$.

The present description also proposes an assembly for controlling at least one container comprising a medical product, at least one container being provided with an electronic tag comprising a memory storing at least one item of information specific to said medical product, the dispenser comprising at least one dispenser as defined above.

A control system for at least one container comprising a medical product is also proposed, at least one container being provided with an electronic tag comprising a memory storing at least one item of information specific to said medical product, the facility comprising the assembly as defined above.

The present description also describes a method for controlling at least one container comprising a medical product, the control method being carried out with the aid of a dispenser comprising a reader, at least one container being provided with an electronic tag comprising a memory storing at least one item of information specific to said medical product, the dispenser comprising multiple inner walls delimiting a storage volume, the multiple inner walls comprising side walls and a bottom wall on which the containers or the package comprising the containers are intended to rest, the side walls delimiting a single access opening to the storage volume, the dispenser being able to receive at least one container or a package comprising at least one container in the storage volume, the method comprising at least the reading by the reader of at least one information item stored in the memory of each electronic label.

For this purpose, this description relates to a mobile control terminal comprising a medical product intended for a single patient, at least one container being provided with an electronic tag comprising a memory storing first data amongst which at least one data item specific to the medical product, the mobile terminal comprising a first barcode reader reading second data on a patient's own identification bracelet, a second reader reading the first data, and a controller comparing the first data and the second data to obtain a comparison result and validating that the medical product is intended for the patient wearing the identification bracelet based on the comparison result.

According to a particular embodiment, the mobile terminal has one or more of the following features, taken alone or in any technically possible combination:

the second reader is an RFID reader.
the mobile terminal is a personal assistant.
the medical product is a drug to be injected to the single patient.
the medical product is a medical device.
the mobile terminal has a memory storing physiological constants specific to the patient.
the mobile terminal includes a communication device interacting with a billing module.

The present description also proposes a control assembly for at least one container containing a medical product, at least one container being provided with an electronic tag comprising a memory storing first data amongst which at least one data specific to the medical product, the assembly comprising a terminal as defined above.

A control system of containers comprising products is also proposed, at least one container being provided with an electronic tag comprising a memory storing first data amongst which at least one specific data to the medical product, the facility comprising an assembly as defined above.

According to a particular embodiment, the facility has one or more of the following features, taken alone or in any technically possible combination:

the facility includes control terminals equipped with a reader that reads the initial data.
the facility includes a dispenser for controlling at least one container comprising a medical product, at least one container being provided with an electronic tag comprising a memory storing at least one specific information to the said medical product, the dispenser comprising multiple inner walls delimiting a storage volume, the multiple inner walls comprising side walls and a bottom wall on which the containers or the package comprising the containers are intended to rest, the side walls delimiting a single access opening to the storage volume, the dispenser being able to receive at least one container or package comprising at least one container in the storage volume; and a reader suitable for reading at least one information stored in the memory of each electronic label, the reader comprising multiple loop-shaped antennas, each side wall comprising a support able to house at least part of one of the antennas.

The present description also describes a method for controlling at least one container comprising a medical product intended for a single patient, at least one container being provided with an electronic tag comprising a memory storing the first data amongst which at least one specific data to the medical product, the method comprising at least the reading of the second data on an identification bracelet specific to a patient, the reading of the first data, and comparing the first data and the second data to obtain a comparison result and validating that the medical product is intended for the patient wearing the identification bracelet based on the comparison result.

BRIEF DESCRIPTION OF THE DRAWINGS

Features and advantages of the invention will appear when reading the following description, given only as a non-limitative example, and made with reference to the attached drawings, in which:

FIGS. 13 to 16 are examples of menus displayed by the mobile terminal.

DETAILED DESCRIPTION OF PARTICULAR EMBODIMENTS

General Description of a Control Facility Intended for an Infrastructure

Figure 1:
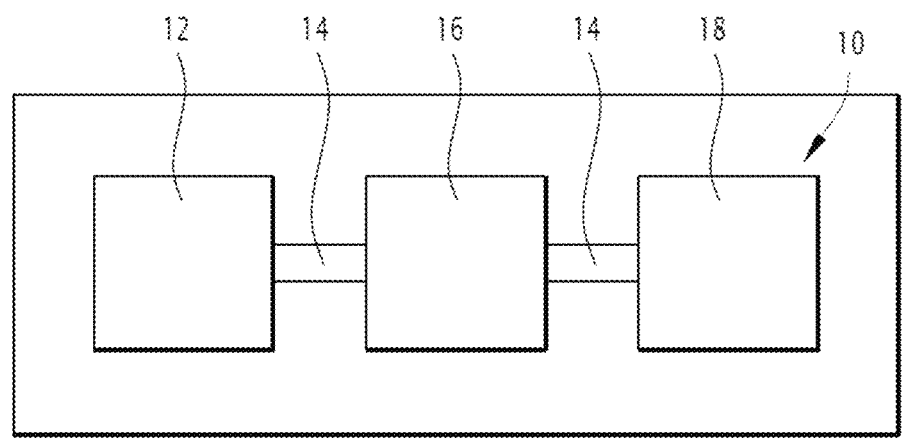
FIG. 1 is a schematic view of a medical infrastructure.

An infrastructure 10 is shown schematically in FIG. 1.

The infrastructure 10 is a medical infrastructure.

In the proposed example, the infrastructure 10 is a hospital complex.

According to other embodiments, the infrastructure 10 is a health care center or a clinic.

Alternatively, the infrastructure 10 is a set of locations for implementing home hospitalization.

More generally, the infrastructure 10 is a set of locations enabling the implementation of one or more medical treatments on at least one patient.

In the case of FIG. 1, the infrastructure 10 comprises a preparation center 12, a transport area 14, a care station 16 and a room 18.

The infrastructure 10 is equipped with a monitoring facility.

The control facility enables the control of at least one container with a medical product for a single patient.

The medical product is, for example, a medicine to be administered to a patient.

The medicine is a magisterial preparation, made for a specific patient, for example following a prescription by name.

The drug is administered to the patient by injection.

The drug is, for example, a compound used in chemotherapy.

Alternatively, the medical product is a contrast agent.

A contrast agent is an agent that artificially increases the contrast in order to better visualize an anatomical structure such as an organ or a pathological condition such as a tumor by medical imaging.

Alternatively, the medical product is a pouch containing biological products, such as blood products (primary blood, plasma, platelets, red blood cells, etc.) or cellular engineering products (cells, stem cells, etc.).

Alternatively, the medical product is an implantable medical device (IMD).

The medical product is, for example, a prosthesis to be placed in a patient, an implant of a part of the body or endoprosthesis such as a stent.

An example of a medical product is an active implantable medical device (AIMD).

The medical product is, for example, a stimulator for a body part such as a pacemaker, lead or pump.

The control facility is based in particular on RFID technology (Radio Frequency Identification, which literally means "radio frequency identification").

The control facility combines an electronic tag (RFID tag) applied to each chemotherapy preparation with tag reading and encoding equipment placed at a strategic point in the circuit and software divided into four modules.

The electronic tag 108 is an electronic tag for wireless communication.

According to the example described, the electronic tag 108 is an RFID chip (from the English "radio frequency identification", in French meaning "identification radiofréquence").

To give an order of magnitude, the RFID chip is a rectangle 35 millimeters (mm) long by 20 mm wide. Nevertheless, the RFID chip is not limited to this geometry and can have variable dimensions and shapes (square, rectangular, round, etc.).

The facility includes multiple assemblies designed to ensure the traceability of containers of chemotherapy preparations from the preparation to the administration to a patient in need of said chemotherapy preparation.

The facility assemblies are intended to be used in combination with commercial software or barcode scanners.

Each assembly is presented in succession in the following with reference to a location in the infrastructure 10.

Four assemblies will thus be described for the case of FIG. 1: a first assembly for the preparation center 12, a second assembly for the transport area 14, a third assembly for the treatment station 16 and a fourth assembly for the room 18.

Description of a First Assembly of the Facility

Figure 2:
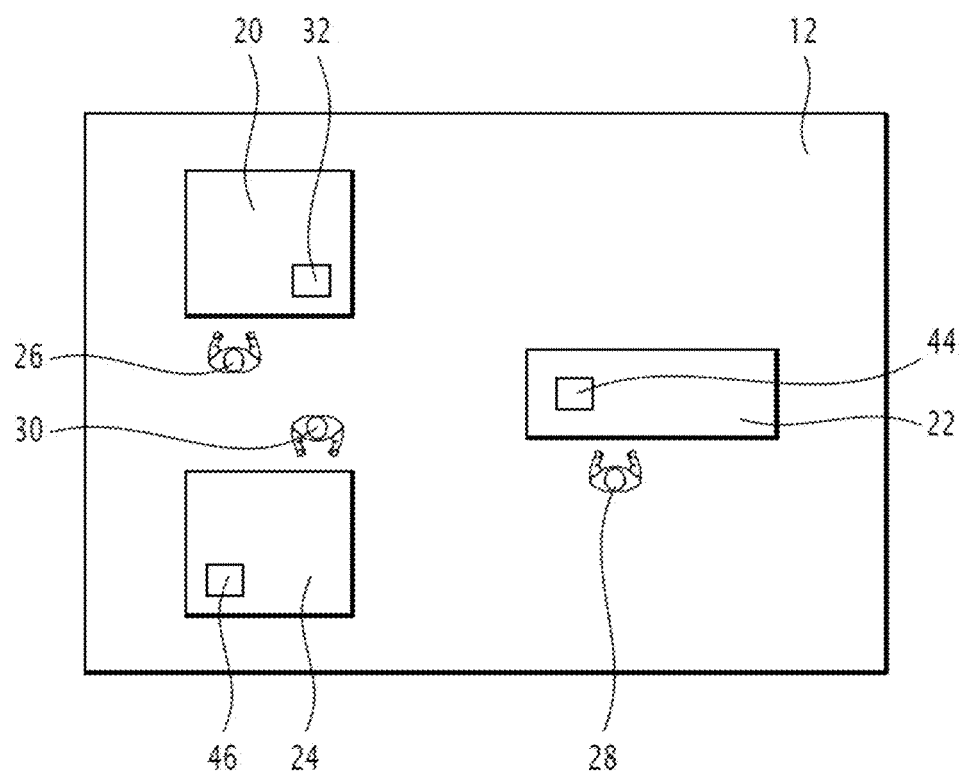
FIG. 2 is a schematic view of a first part of the medical infrastructure of FIG. 1.

To describe the first assembly, the preparation center 12 is described with reference to FIGS. 2 and 3.

The preparation center 12 has three stations 20, 22 and 24 used by an operator 26, 28 and 30 respectively.

The first station 20 is an initialization station 20.

In the initialization station 20, the first operator 22 carries out a series of interventions using a first workstation 32 to initialize a container 34.

The container 34 is a container for chemotherapy preparations.

For example, the container is a pouch or a syringe.

Figure 3:
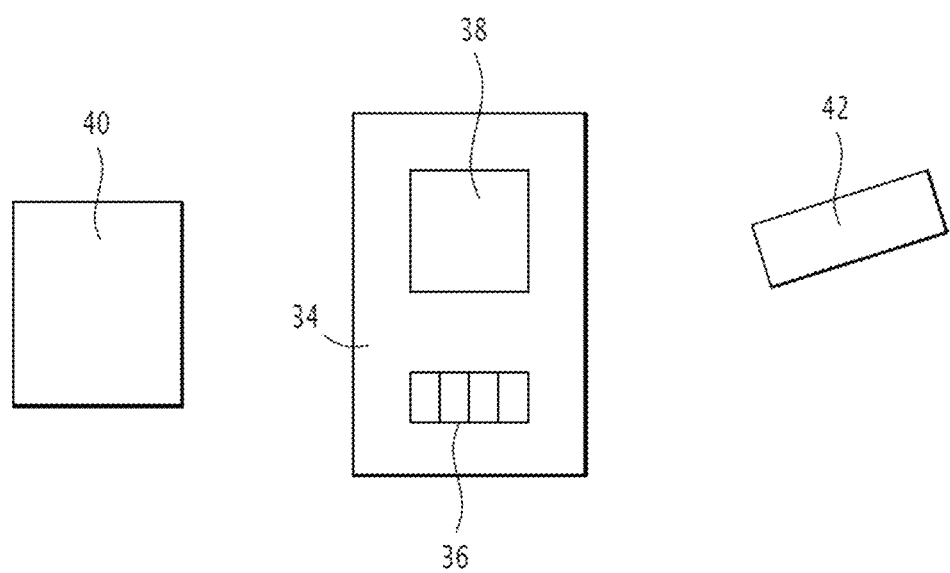
FIG. 3 is a schematic representation of an apparatus of the first part of the medical infrastructure in FIG. 2.

As can be seen in FIG. 3, the container 34 is provided with a barcode 36 and tag 38.

The tag 38 has been obtained by a printer which, according to a particular embodiment, is part of the first workstation 32.

To interact with the container 34, the first workstation 32 is equipped with a computer 40 and a reader 42.

The tag 38 is an RFID tag.

The computer 40 and computer software are able to interact to implement a control method for one or more containers.

More generally, the computer 40 is an electronic computer that is able to manipulate and/or transform data represented as electronic or physical quantities in computer registers and/or memories into other similar data corresponding to physical data in memories, registers or other types of display, transmission or storage devices.

The computer 40 has a processor comprising a data processing unit, memories and a media drive. The computer 40 also includes a keyboard and display unit.

The computer program product comprises a readable information medium.

A readable information medium is a medium that can be read by the computer 40, usually by the reader. The readable information medium is a medium suitable for storing electronic instructions and capable of being coupled to a bus of a computer system.

For example, a readable information medium is a floppy disk, optical disk, CD-ROM, magneto-optical disk, ROM, RAM, EPROM, EEPROM, magnetic card or optical card.

On the readable information medium, a first computer program with program instructions is stored. The first computer program is the first module of the four above-mentioned modules.

The computer program can be loaded onto the data processing unit and is suitable for the implementation of the control method.

The reader 42 is able to read information from the tag 38 as well as writing information to the tag 38.

In this sense, the reader 42 is a RFID reader.

The second station 22 is a preparation station 22.

The preparation station 22 is equipped with a drug manufacturing device 44.

For example, the manufacturing device 44 has a sterile part to which the second operator 28 has access by using gloves.

The third station 24 is a dispatch station 24.

The preparation station 24 has a second mobile station 46.

In operation, at the first station 20, the first workstation 32 enables a first operator 26 to log on by scanning a badge on a reader. The computer screen displays the operator's account.

Each container 34 is prepared and equipped with an RFID tag is placed on a reader and scanned to ensure that the tag is empty.

The operator is then prompted to scan the barcode of the container 34.

The container 34 is then used at the second station 22 by a second operator 28 to put the chemotherapy preparation inside the container 34.

A third operator 30 writes the name of the person who prepared the container, the preparation contained in it and the name of the associated patient in the memory of the RFID tag.

The container 34 is assigned the status of "prepared".

In general, multiple items of information may be present on the tag, including the product's prescription number, the product's international non-proprietary name, the product's dose, the product's expiration date, the product's route of administration or the product's intended use.

The first assembly thus makes it possible to obtain a container 34 in the prepared state.

Description of a Second Assembly of the Facility

Description of a Dispenser

Figure 4:
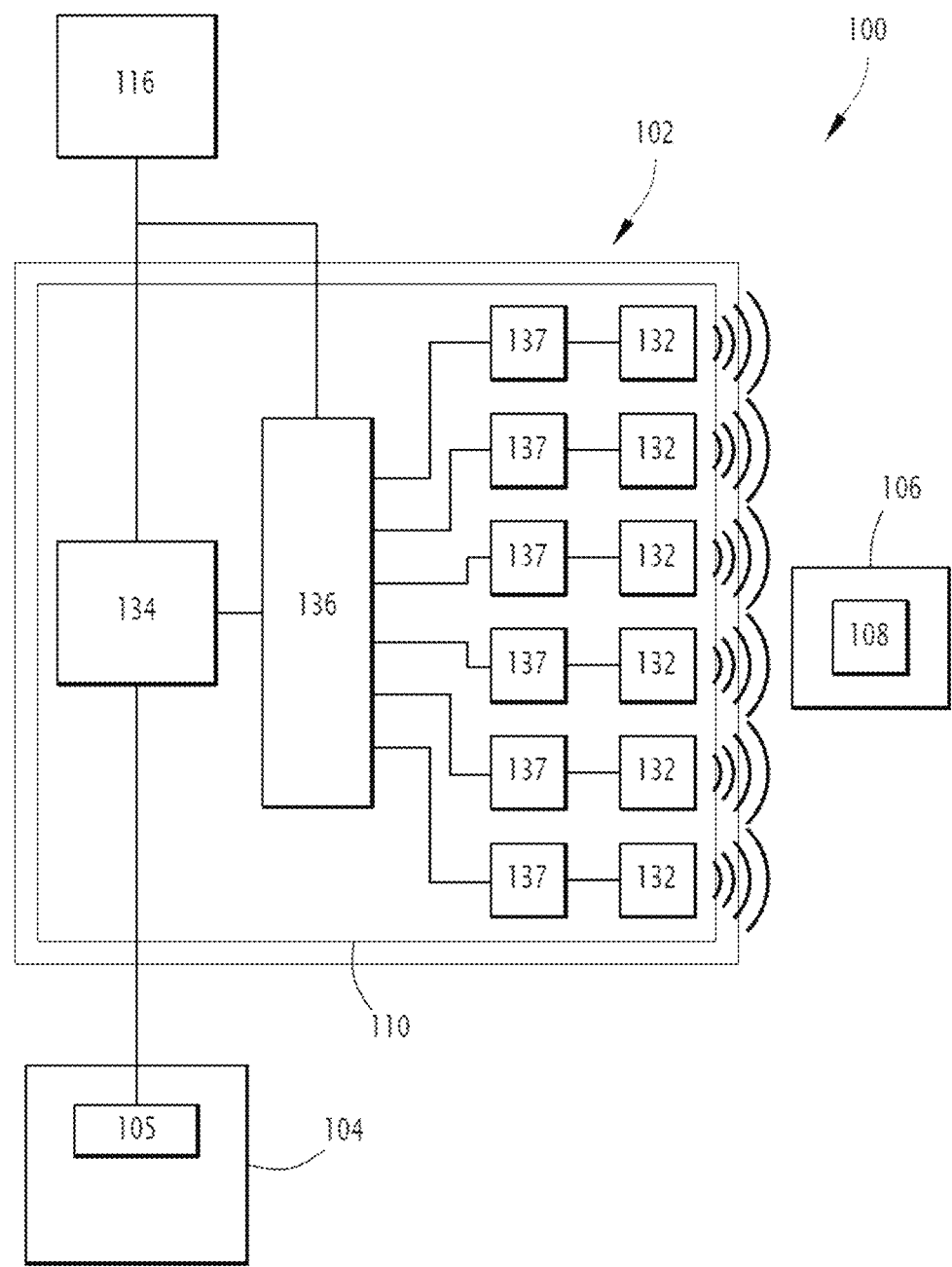
FIG. 4 is a schematic representation of a dispenser.

An example of the dispenser 100 is shown in FIG. 4.

The dispenser 100 comprises at least one receiving part 102 and at least one controller 104.

The controller 104 is adapted to communicate with at least one receiving part 102. The receiving part 102 is also capable of communicating with the controller 104.

The controller 104 and receiving part 102 communicate over a wireless link.

For example, the controller 104 and the receiving part 102 communicate using the packet-switched LAN protocol, such as an ethernet protocol.

The controller 104 includes a human-machine interface 105 that can control the receiving part 102 and display at least one information item read by the receiving part 102.

The HMI 105 includes, for example, a display.

According to a particular embodiment, the screen is touch-sensitive so that an operator is able to interact with the receiving part 102, for example by validating the displayed information. The touch screen is compatible with gloves.

Figure 5:
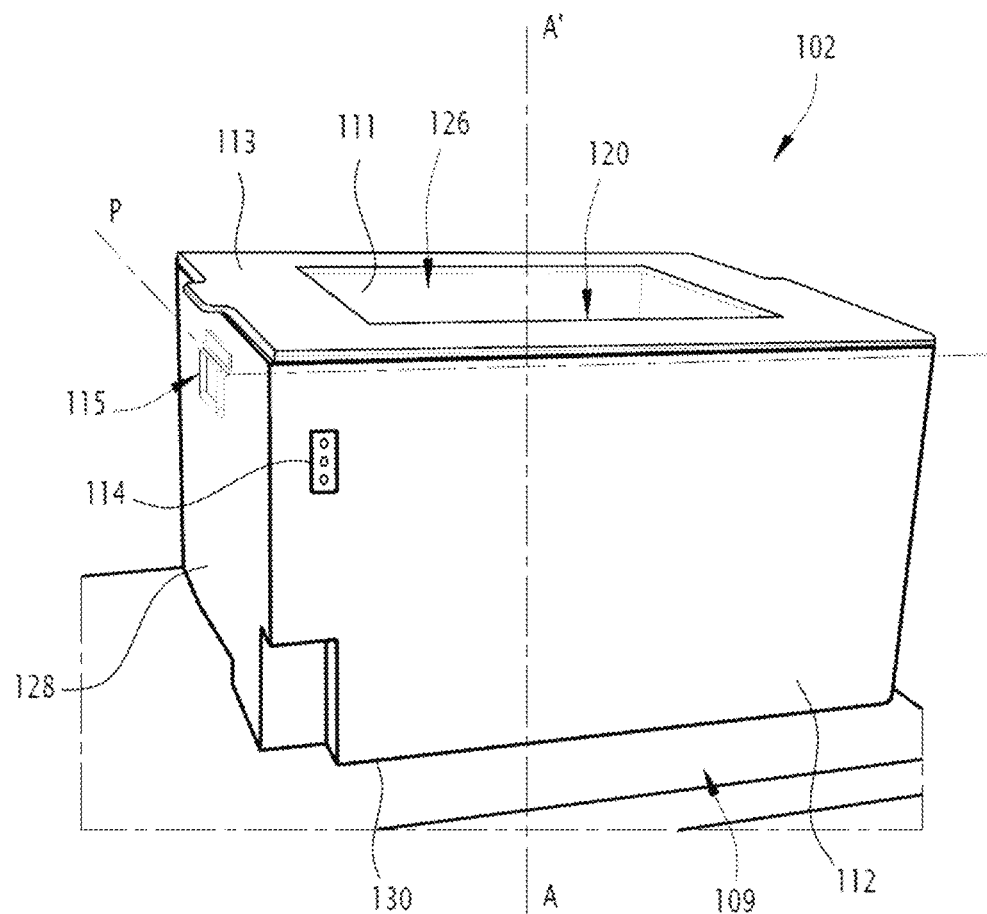
FIG. 5 is a perspective view of an example of the dispenser.
Figure 6:
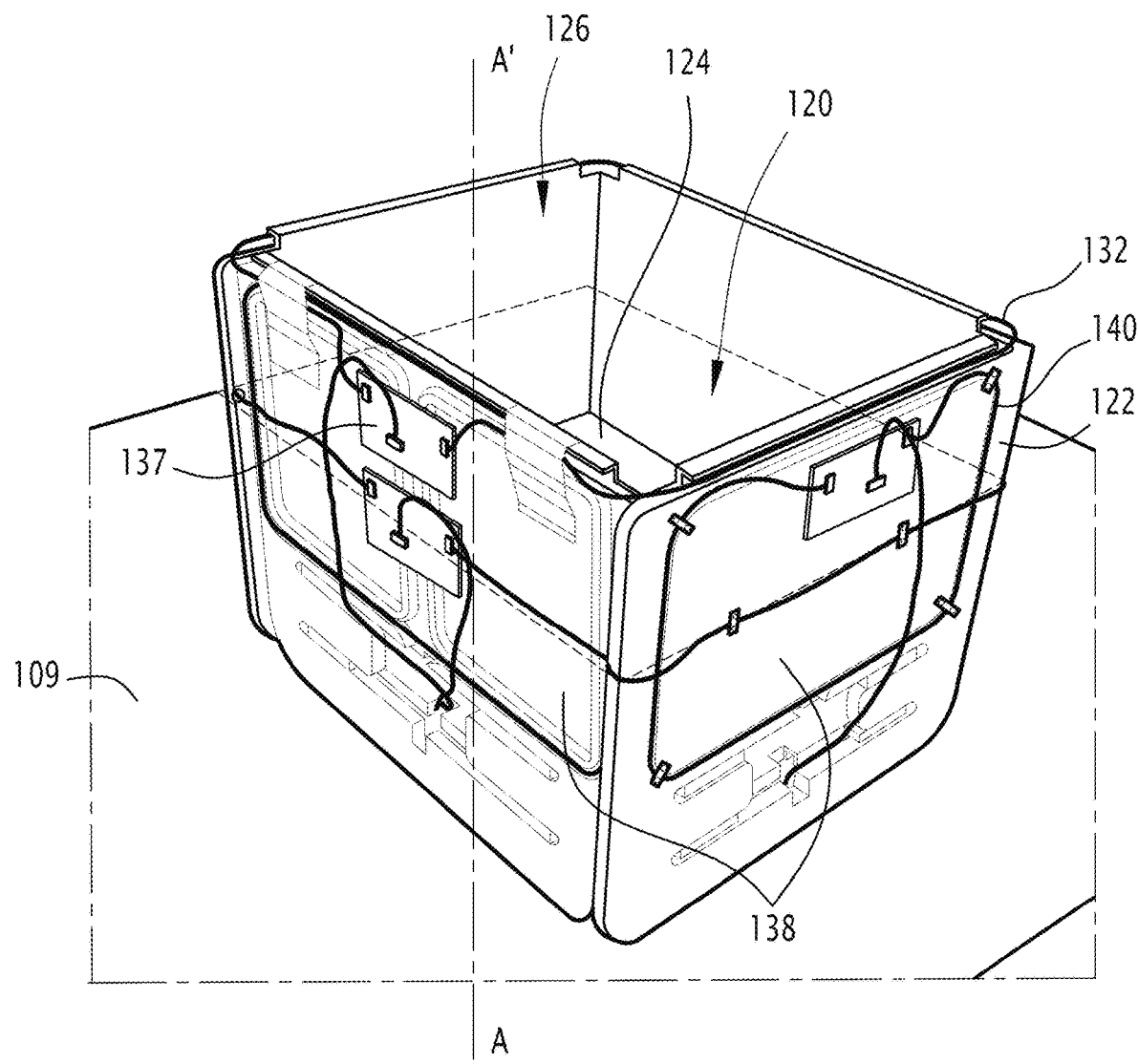
FIG. 6 is a perspective view of the dispenser in FIG. 5 without the external walls.

FIGS. 5 and 6 show examples of partial or total views of the receiving part 102.

The dispenser 100 is configured to control at least one container 106.

The receiving part 102 is capable of receiving at least one container 106 or a package containing at least one container 106.

The receiving part 102 is suitable for resting on a supporting surface 109 such as a table for example.

In the following, the terms "vertical" and "horizontal" refer to the supporting surface 109. In particular, "vertical" is understood to be perpendicular to the supporting surface 109.

The receiving part 102 consists of a reader 110 and multiple walls.

The multiple walls comprise multiple inner walls 111, multiple outer walls 112 and connecting walls 113.

The receiving part 102, in the example in FIG. 5, additionally comprises an indicating device 114 and a pair of handles 115 for moving the dispenser 102.

The receiving part 102 is electrically powered by the mains 116.

In the example in FIG. 5, the receiving part 102 consists of five inner walls 111 and five outer walls 112.

The inner walls 111 are made of plastic, such as polyethylene or polypropylene.

The inner walls 111 delimit a storage volume 120.

The storage volume 120, in the example in FIG. 5, is parallelepiped in shape.

The receiving part 102 is suitable for receiving at least one container 106 or a package containing at least one container 106 in the storage volume 120.

The storage volume 120 has a volume of between 0.015 cubic meters ($m^3$) and 0.03 $m^3$, for example 0.022 $m^3$.

The ratio between the storage volume 120 and the volume of the receiving part 102 is between 20% and 30%, for example 25%.

The inner walls 111 comprise the inner side walls 122, here four inner side walls 122, and an inner bottom wall 124 on which the containers 106 or the package comprising the containers 106 are intended to rest.

The lower wall 124 extends in a horizontal plane.

The height of the inner bottom wall 124 in relation to the support surface 109 of the receiving part 102 is between 50 mm and 150 mm, such as 117 mm.

Each inner side wall 122 extends in a vertical plane perpendicularly from one side of the inner bottom wall 124.

Each inner side wall 122 has a height along the A-A' vertical axis of between 200 mm and 300 mm, such as 218 mm.

Each inner sidewall 122 has a length in the horizontal direction of between 300 mm and 500 mm, such as 282 mm or 355 mm.

As can be seen in FIG. 6, the inner side walls 122 delimit a single access opening 126 to the storage volume 120.

The receiving part 102 therefore does not have an access opening to the storage volume 120 through it.

The access opening 126 defines an opening plane P.

The opening plane P is a horizontal plane, perpendicular to the A-A' axis.

The outer walls 112 form the outer structure of the receiving part 102.

As can be seen in FIG. 5, the receiving part 102 is a parallelepiped-shaped structure.

Each outer wall 112 is made of an electrically conductive material with an electrical conductivity greater than or equal to 0.3 mega Siemens per cm ($MS/cm^{-1}$).

For example, each outer wall 112 is made of aluminum.

The outer walls 112 thus act as electromagnetic isolation of the inside of the receiving part 102.

The outer walls 112 delimit an inner volume. The inner volume is equal to the volume of the receiving part 102.

The receiving part 102 has a volume of less than 0.1 $m^3$, such as 0.095 $m^3$.

The storage volume 120 is arranged in the inner volume.

The outer walls 112 consist of outer side walls 128, here four outer side walls 128, and an outer bottom wall 130.

The receiving part 102 is suitable for resting on the contact surface 109 via the outer bottom wall 130.

The outer bottom wall 130 extends in a horizontal plane.

Each outer side wall 128 extends in a vertical plane perpendicularly from one side of the outer bottom wall 130.

Each outer side wall 128 has a height along the A-A' vertical axis of between 300 mm and 400 mm, such as 335 mm.

Each outer side wall 128 has a length in a horizontal direction of between 400 mm and 600 mm, such as 480 mm or 588 mm.

In the example in FIG. 5, two of the outer side walls 130 are parallel to two of the inner side walls 122. The other two outer side walls 130 are parallel to the other two inner side walls 122.

The connecting walls 113 connect the free ends of the inner side walls 122 and the outer side walls 130.

The reader 110 is capable of reading at least one information item stored in the memory of each electronic tag 108.

In particular, the reader 110 is capable of simultaneously reading at least one information item stored in the memory of at least twenty electronic tags 108.

"Simultaneously" means reading following the same electromagnetic pulse emitted by the reader 110.

The reader 110 is able to operate according to a communication protocol adapted to read at least one information item stored in the memory of each electronic tag 108. The communication protocol is, for example, an RFID communication protocol.

The reader 110 is able to transmit or receive a signal with a frequency between 13.540 mega Hertz (MHz) and 13.567 MHz.

The reader 110 includes multiple antennas 132.

The reader 110 also includes at least one reader module 134 and a multiplexer 136.

The multiplexer 136 connects the antennas 132 to the reader module 134.

The reader module 134 is configured to read at least one information item stored in the memory of each electronic tag 108 and to send a signal comprising at least one information item to the external controller 104 at the receiving part 102.

The reader 110 also includes, for each antenna 132, an antenna adapter 137 located between the antenna 132 and the multiplexer 136.

The antenna adapter 137 optimizes the power transfer between an antenna 132 and the rest of the reader 110 by modulating the impedance of the reader 110.

The antenna adapter 137 can be adjusted manually, for example by means of a dial.

Each antenna 132 is in the form of a loop.

Each antenna 132 defines an inner surface. The inner surface of each antenna 132 is greater than or equal to 0.04 m$^2$.

Each antenna 132 is capable of creating a magnetic field oriented in one direction.

Each antenna 132 is a coaxial cable. The coaxial cable is a cable with two conductors of opposite poles separated by insulation.

For example, the coaxial cable is of the RG58 type, which is well known to the person skilled in the art.

Each inner sidewall 122 has a support 138 able to house at least part of one of the antennas 132.

For example, the support 138 is a flange screwed onto the inner side wall 122.

Together with the inner side wall 122, the bracket 138 defines a passage section for antenna 132.

In particular, each inner side wall 122 receives at least one antenna 132, the so-called side antenna 140.

Each side antenna 140 is attached to the outer surface of the associated inner side wall 122.

The ratio between the inner surface of each side antenna 140 and the surface of the associated inner side wall 122 is greater than or equal to 75%.

Figure 7:
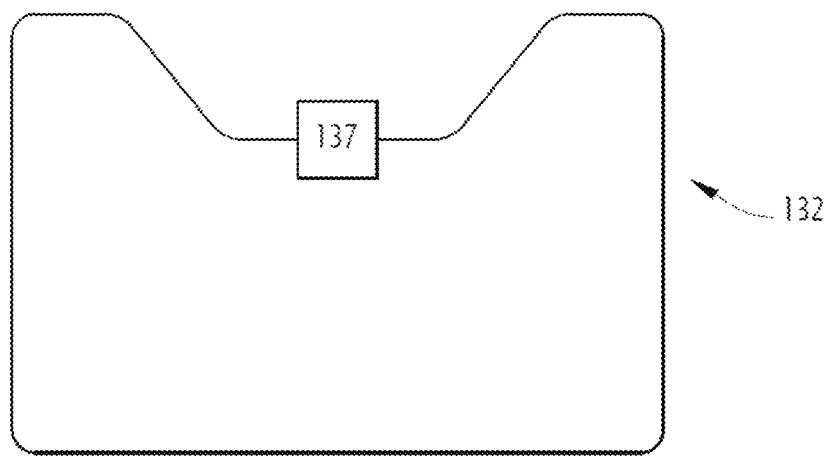
FIG. 7 is a schematic view of a side antenna that is part of the dispenser in FIG. 5.
Figure 8:
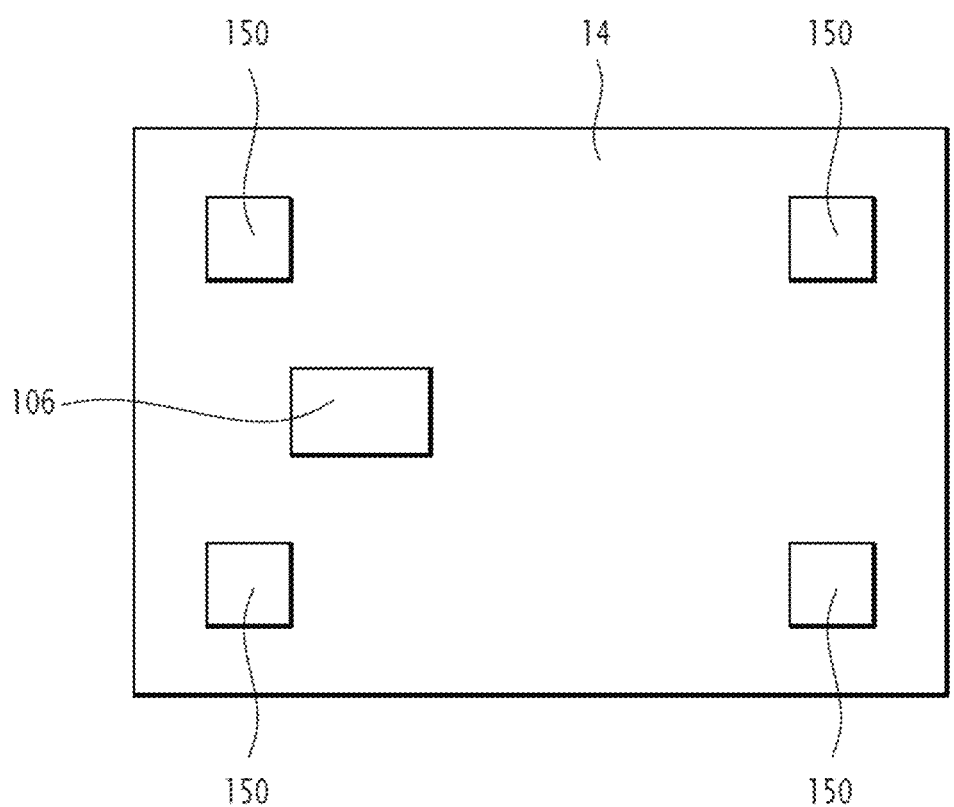
FIG. 8 is a schematic view of a second part of the medical infrastructure in FIG. 1.

As shown in FIG. 7, each side antenna 140 has, for example, the shape of a rectangle with rounded corners.

One side of the rectangle forms a sinusoid towards the inside of the rectangle, with the side antenna 140 being connected to its respective antenna adapter 137 at the sinusoid.

In particular, the said side has five gaps.

The first gap extends from one corner of the rectangle.

The first gap is perpendicular to the adjacent side of the rectangle.

The second gap extends from the first gap. The first gap and the second gap are connected by a first rounded joint.

The second gap forms an angle between 30 degrees (°) and 60 degrees (°) with the first gap.

The third gap extends from the second gap. The second gap and the third gap are connected by a second rounded seam.

The third gap is parallel to the first gap.

The third gap is connected to the associated antenna adapter 137.

The fourth gap extends from the third gap. The third gap and the fourth gap are connected by a third round connector.

The fourth gap forms an angle of between 30° and 60° with the third gap.

The fifth gap extends from the fourth gap. The fifth gap and the fourth gap are connected by a fourth rounded junction.

The fifth gap is parallel to the third gap and extends from the first gap.

The fifth gap is connected to a corner of the rectangle.

The fifth gap is perpendicular to the adjacent side of the rectangle.

At least one antenna 132 is arranged on all inner side walls 122 and extends in the opening plane P. Said antenna 132 is arranged around the access opening 126.

At least one antenna 132 is arranged on all side walls at a distance from the opening plane P. The antenna 132 extends, for example, in a plane parallel to the opening plane P. The antenna 132 extends, for example, in a horizontal plane with a height of 200 mm to 250 mm, such as 223 mm, in relation to the support surface 109.

The indicating device 114 is able to emit a signal when the receiving part 102 is connected to a power supply.

The indicating device 114 is also able to send a signal when the reader 110 is reading at least one electronic tag 108.

In addition, the indicating device 114 is able to output a signal based on the information read from each electronic tag 108.

In a particular embodiment, the indicating device 114 is a luminous device. For example, the indicating device 114 has three LED lamps of different colors.

Each handle 115 is attached to an outer side wall 128 by means of screws, for example.

Each handle 115 is suitable to be grasped by the hand of an operator who wants to carry the receiving part 102. The two handles 115 are arranged on two parallel outer side walls 128.

The operation of the dispenser 100 is now explained with reference to an example of the implementation of a method for controlling at least one container 106 containing a medical product by means of a control system 100.

Multiple containers 106 are to be checked.

For example, twenty containers 106 are to be checked.

The multiple containers 106 is placed in the storage volume 120 of the receiving part 102 by an operator.

Alternatively, the multiple containers 106 are placed in a package and the package is placed in storage volume 120 by the operator.

The operator uses the human-machine interface 105 to the instruct reader 110 to read the electronic labels 108 present in the receiving part 102.

The control method then includes a step in which the reader 110 reads at least one information item stored in the memory of each electronic tag 108.

In particular, the reading is carried out by the reading module 134 from the signals sent by the six antennas 132 via the multiplexer 136.

The read module 134 then sends a signal containing at least one information item to the controller 104.

At least one information items displayed on the human-machine interface 105.

If the information is validated by the operator or by the controller 104, the containers 106 are considered valid and the status of each container 106 is changed from "prepared" to "dispensed".

The valid containers 106 are then, for example, sent to a health center to treat a patient.

Otherwise, the containers 106 with invalid information are set aside by the operator.

Multiple variants of the dispenser 100 are possible.

According to a variant, the display of the human-machine interface 105 has a keyboard or buttons.

In another variant, the dispenser 100 is powered by its own power supply, such as a battery.

In another variant, the antenna adapter 137 can be adjusted automatically.

According to another variant, multiple variants of the antenna shape 132 are possible depending on the type of the electronic labels 108. For example, each antenna 132 has a circular or square shape.

In another variant, the indicating device 114 is a sound device.

Description of a Specific Example of use of the Dispenser with other Elements

The dispenser 100 described above has been proposed for use alone.

However, the dispenser 100 is best used in combination with other components to form the second assembly.

Figure 9:
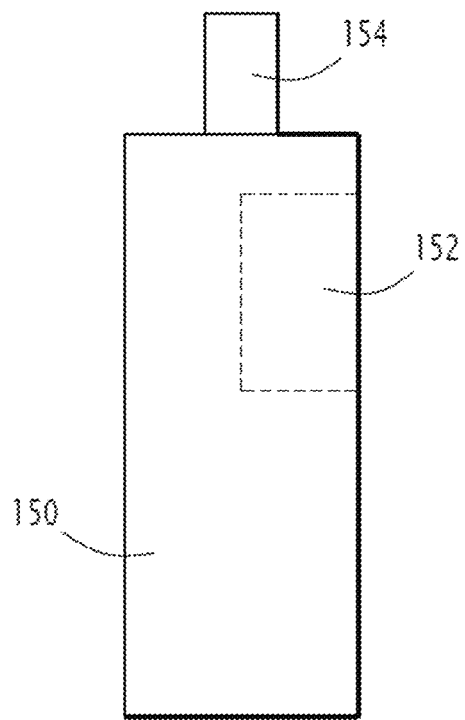
FIG. 9 is a schematic representation of a terminal forming part of the second part of FIG. 8.

As shown in FIG. 9, the second assembly consists of a dispenser 100 and four control terminals 150 equipped with an RFID reader.

A control station 150 is detailed in FIG. 9.

The control station 150 has an antenna 152 and a warning device 154.

The antenna 152 is used to read the tag 38.

The display screen 154 is used to warn if an anomaly is detected.

For example, if the control station 150 is used as a computer interacting with one of the four modules mentioned above, the dispenser 100 is connected to the control station 150. A destination for the containers is entered by the user.

Once the containers to be distributed to the entered destination are placed in the dispenser 100, all the tags are read. The control terminal 150 displays the destination and status for each container 34. If the destination is correct, the data for the container 34 appears in green. If the destination is incorrect, the data for the container 34 appears in red and the dispensing of all containers 34 is blocked. The user is then prompted to remove the wrong container 34 or the wrong containers 34 to continue dispensing.

The status of the container 34 is changed from "prepared" to "dispensed" with one click.

This enables group dispensing of up to 20 products at the same time.

The facility provides real-time information to the logistics and treatment rooms.

The facility also enables the secure management of returns and reassignments.

The four above-mentioned modules are updated in real time, which enables following the routing of the preparations after dispensing.

Dispensing can also take place at the preparation center 12. In such a case, the second assembly aims to track the package from the preparation center 12 to the care station 16.

The status for the container 34 is then "picked up" or "delivered".

Such an assembly thus enables tracking the departures and arrivals in real time from departure to arrival. This avoids any routing errors.

Description of a Third Assembly of the Facility

Figure 10:
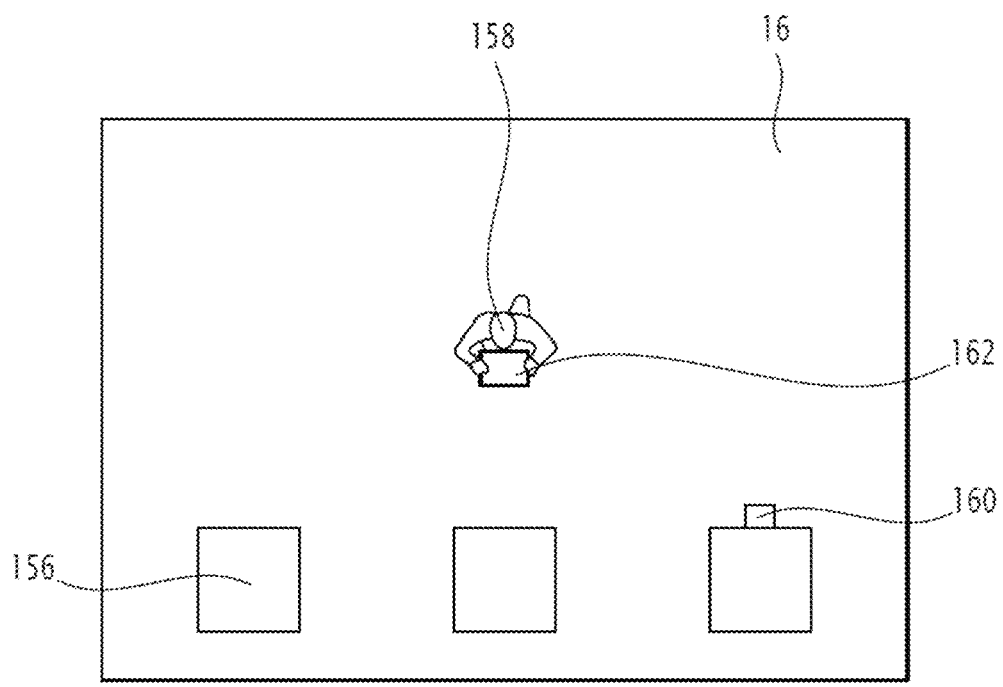
FIG. 10 is a schematic view of a third part of the medical infrastructure in FIG. 1.

FIG. 10 shows a care station 16 equipped with storage cabinets 156 for storing medical products.

An operator 158 carries a tablet 160 equipped with an RFID reader and interacting with a central computer 162.

The operation is similar to the previous operation, that is, the display on the tablet 160 shows the container data in green if the correct container has reached the correct destination.

When a problem occurs, for example the patient no longer needs treatment, it is possible to return the container 34 to a pharmacy and assign it to a different patient.

The new statuses are "received", "not administered" and "to be returned".

This makes it possible to track the status and routing of the preparations in real time.

This makes it possible to automate incoming inspection.

The facility offers the possibility of programming the return of a preparation.

Description of a Fourth Assembly of the Facility

Figure 11:
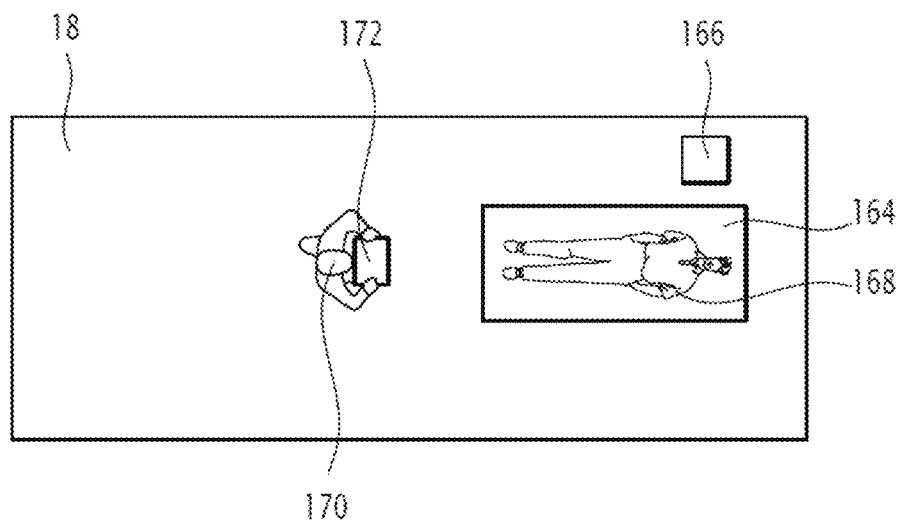
FIG. 11 is a schematic view of a fourth part of the medical infrastructure in FIG. 1.

To describe the fourth assembly, the room 18 is described with reference to FIG. 11.

The room 18 has a bed 164 and a product delivery column 166.

A patient 168 is lying on the bed 164.

A medical operator 170 is also present. The medical operator 170 is attempting to administer the chemotherapy preparation to the patient 168.

The medical operator 170 is, for example, a nurse.

The operator 170 has a mobile terminal in the form of a personal assistant 172.

Figure 12:
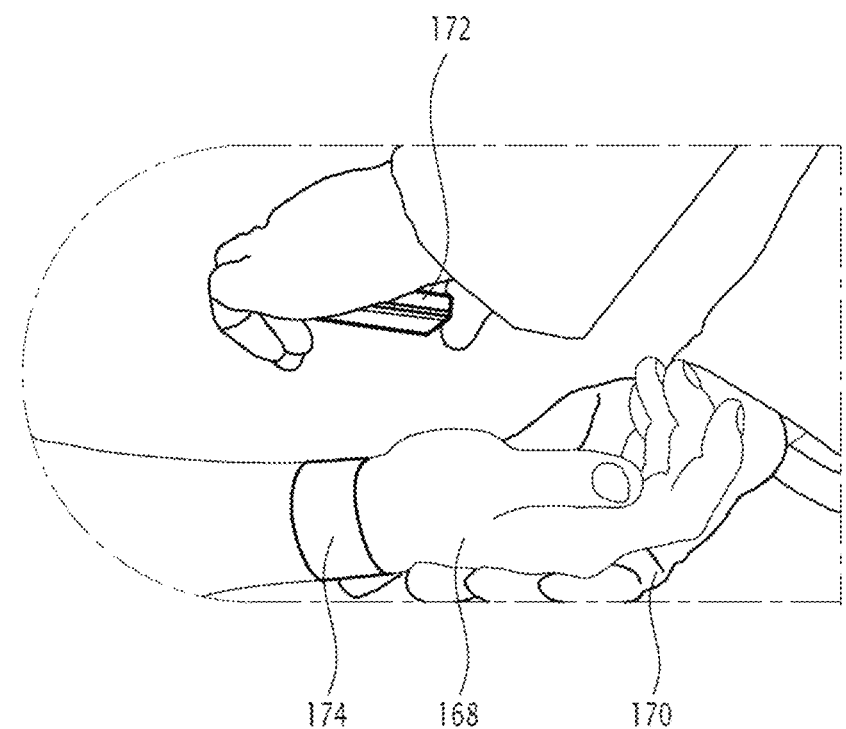
FIG. 12 is a representation of a mobile terminal operating in the fourth part of the medical infrastructure.

As can be seen in FIG. 12, the patient 168 is wearing an identification bracelet 174.

The identification bracelet 174 is provided with an identification code specific to the patient 168.

The identification code is in the form of a barcode and contains second data 192.

The personal assistant 172 communicates with a central server using a wireless communication protocol.

The personal assistant 172 is able to provide the medical operator 170 with a number of functionalities which are described in reference to FIGS. 13 to 16 showing several menus.

The personal assistant 172 includes a first barcode reader reading the second data on a patient-specific identification bracelet, a second reader reading the first data, and a controller comparing the first and second data to obtain a comparison result and validating that the medical product is intended for the patient wearing the identification bracelet based on the comparison result.

Figure 14:
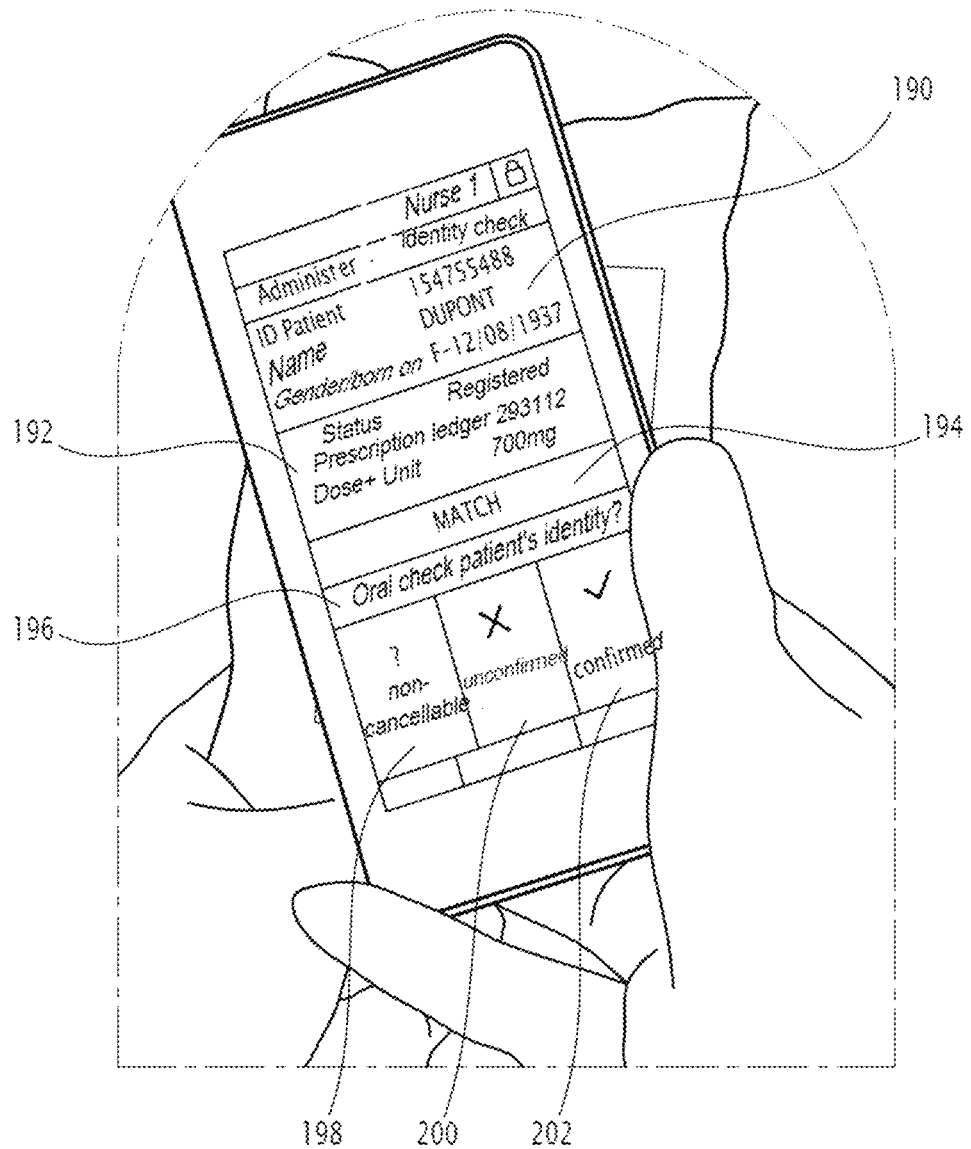

This is shown by a menu visible in FIG. 14.

In this menu, the first data 190 and second data 192 are displayed.

The first data 190 is the data from the RFID reader of the tag of the chemotherapy preparation.

The second data 192 is the data from the barcode reading of the identification bracelet 174 of the patient 168.

In addition, the menu includes multiple interactive zones: an area 196 asking the operator 170 if the verbal check of the identity of patient 168 has been carried out, a button 198 indicating that the check is not possible, a button 200 indicating that the identity of patient 168 has not been confirmed and a button 202 indicating that the identity of patient 168 has been confirmed.

The personal assistant 172 displays "MATCH" in the area 194 in FIG. 14 when the correct container 34 is assigned to the correct patient. Otherwise, the personal assistant 172 displays "STOP" in the area 194. The personal assistant 172 displays the time remaining for administration. At the end of the administration or during the administration if necessary, the operator 170 scans the container 34 again to stop the administration.

The new statuses are "in the course of administration" and "administered".

Optionally, the personal assistant 172 can offer additional functionality.

Figure 13:
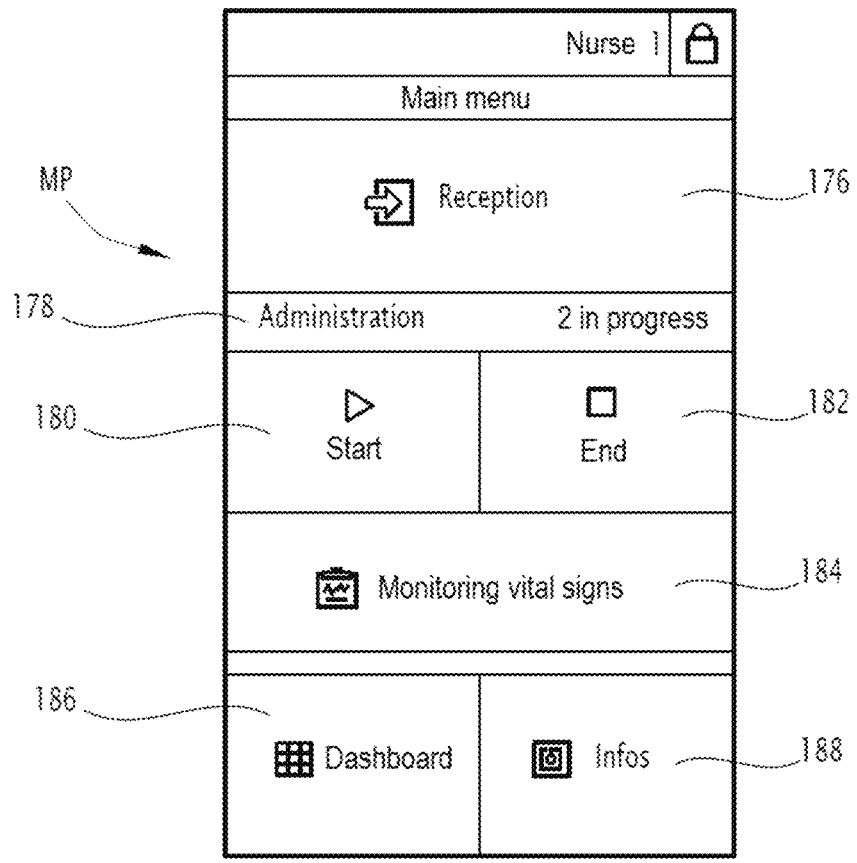

These features are shown by looking at the main menu MM shown in FIG. 13.

The main menu MM has a number of interactive areas: a reception area 176, a display of administrations in progress 178, a start trigger action 180, an end trigger action 182, a constant monitoring access button 184, a dashboard access button 186 and an information access button 188.

A first functionality is to enable the recording of physiological constants.

The recording can be reproduced in graphical form.

Figure 15:
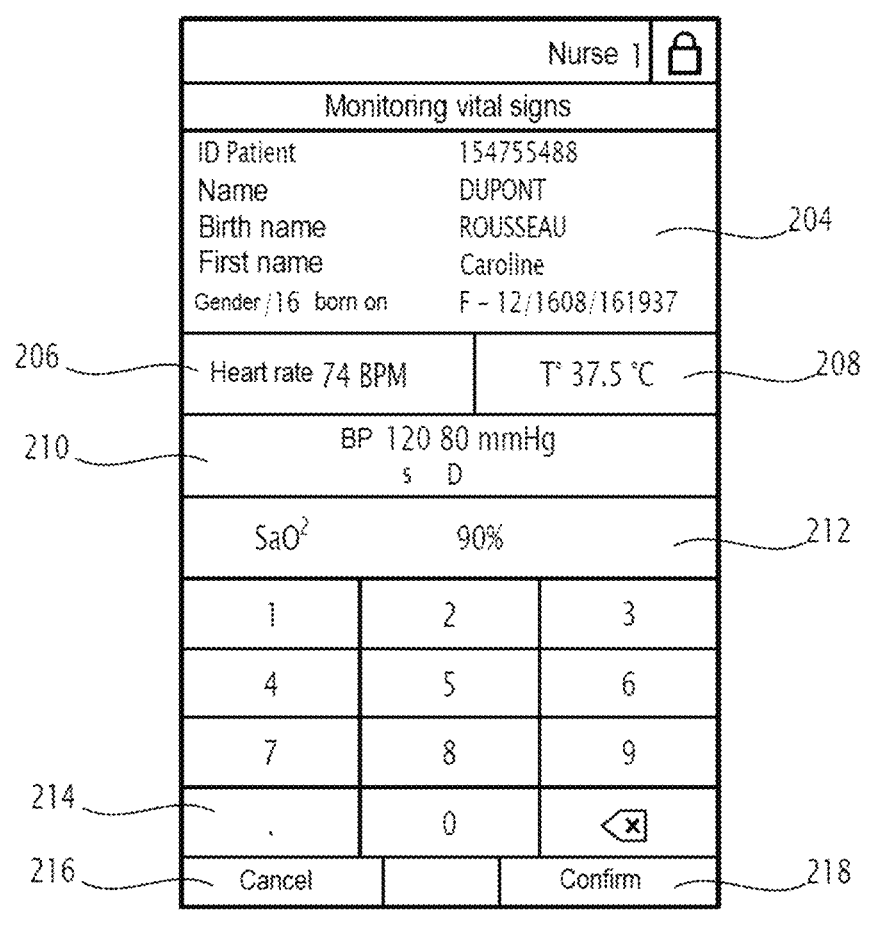

The associated constant monitoring menu is shown in FIG. 15.

The monitoring menu comprises a number of interactive fields: a field 204 for displaying the first data 190, an area 206 for entering the pulse rate of the patient 168, an area 208 for entering the temperature of the patient 168, an area 210 for entering the blood pressure of the patient 168, an area 212 for entering the arterial oxygen saturation of the patient 168, a numerical keypad 214 for entering the data in the areas 206 to 212, a cancel button 216 and a button 218 for validating the entered data.

Alternatively, the areas 206 to 212 can display data for the patient 168, with data for the patient 168 stored in a database. In particular, the area 206 is used to consult the pulse rate of the patient 168, the area 208 is used to consult the temperature of the patient 168, the area 210 is used to consult the blood pressure of the patient 168, the area 212 is used to consult the arterial oxygen saturation of the patient 168.

A second functionality is to organize the work, the administration follow-up being managed by the operator 170.

Figure 16:
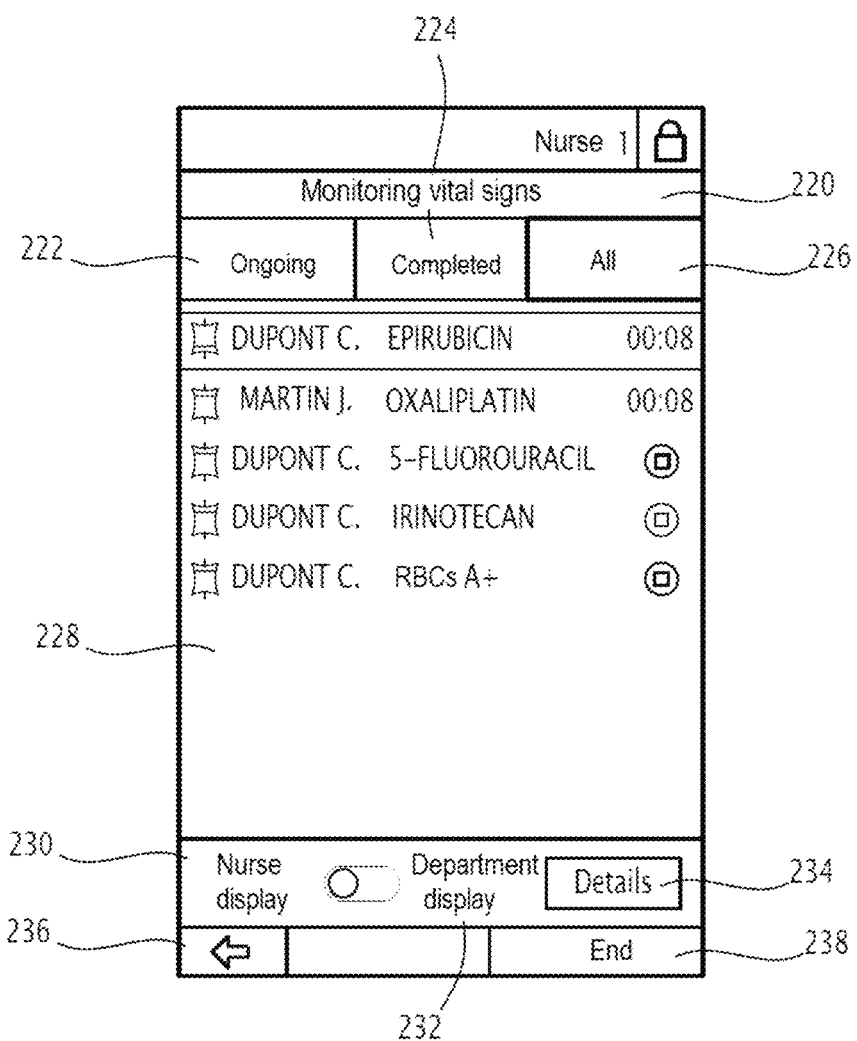

The dashboard menu is visible in FIG. 16.

The dashboard menu consists of a number of interactive areas: an area 220 showing the menu title, a button 222 displaying all patients 168 for whom administration of the product is in progress, a button 224 displaying all patients 168 for whom administration of the product has been completed, a button 226 displaying all patients 168, a display area 228 displaying the patients 168 selected using buttons 222 to 226 as well as the product administered and the time remaining.

The dashboard menu also includes a button 230 to toggle the display in the 228 area between the patients 168 of a given operator 170 and all patients 168 treated by the department, a button 234 to display the first data 1490 associated with a patient 18 selected in the display area 228, a button 236 to return to the previous menu and a button 238 to close the menu.

A third feature is to trigger billing. To do this, the personal assistant 172 includes a communication device that interacts with a billing module.

The use of the fourth assembly ensures that the right product is administered to the right patient.

Conclusion

The facility ensures the traceability of medical preparation containers at every moment from preparation to administration.

The facility enables optimizing and securing the routing of chemotherapy preparations.

The facility is simple to implement.

The facility can be adapted to all types of establishments having chemotherapy activity and even with home hospitalization.

The facility provides enhanced traceability and security.

The facility also enables the optimization of logistics, especially in terms of efficiency and time saving.

From the staff's point of view, it relieves them of certain administrative tasks so that they can maximize the time they spend with patients, as well as eliminating stressful situations due to the risk of administration errors.

The result is better cost control.

This makes it possible to monitor the progress of administrations at any time.

It should be noted that the facility does not require a connection to the institution's computer network.

With the facility not precluding the product type, the facility is also compatible with transfusion.

The invention concerns the combination of all technically possible embodiments.

The invention claimed is:

1. A dispenser for controlling at least one container comprising a medical product, the at least one container being provided with an electronic tag comprising a memory storing at least one information item specific to said medical product, the dispenser comprising:
a plurality of inner walls delimiting a storage volume, the plurality of inner walls comprising side walls and a lower wall on which the containers or the parcel comprising the containers are intended to rest, the side walls delimiting a single access opening to the storage volume, the dispenser being able to receive the at least one container or a parcel comprising the at least one container in the storage volume; and
a reader able to read the at least one information item stored in the memory of each electronic tag, the reader comprising a plurality of loop-shaped antennas, each side wall including a support which is able to house at least part of one of the antennas,
wherein the plurality of walls comprises outer walls, each outer wall being made from an electrically conductive material having an electrical conductivity greater than or equal to 0.3 $MS.cm^{-1}$, the outer walls delimiting an inner volume, the storage volume being arranged in the inner volume.

2. The dispenser according to claim 1, wherein the reader comprises at least four side antennas, each side wall receiving at least one side antenna.

3. The dispenser according to claim 2, wherein each antenna defines an inner surface, the ratio between the inner surface of each side antenna and the surface of the associated side wall being greater than or equal to 75%.

4. The dispenser according to claim 3, wherein the access opening defines an opening plane, at least one antenna being arranged on all of the side walls and extending in the opening plane, and at least one antenna being arranged on all of the side walls separated from the opening plane.

5. The dispenser according to claim 3, wherein the inner walls are made from plastic.

6. The dispenser according to claim 2, wherein each antenna is a coaxial cable.

7. The dispenser according to claim 3, wherein each antenna is a coaxial cable.

8. The dispenser according to claim 2, wherein the access opening defines an opening plane, at least one antenna being arranged on all of the side walls and extending in the opening plane, and at least one antenna being arranged on all of the side walls separated from the opening plane.

9. The dispenser according to claim 2, wherein the inner walls are made from plastic.

10. The dispenser according to claim 1, wherein the access opening defines an opening plane, at least one antenna being arranged on all of the side walls and extending in the opening plane, and at least one antenna being arranged on all of the side walls separated from the opening plane.

11. The dispenser according to claim 10, wherein the inner walls are made from plastic.

12. The dispenser according to claim 1, wherein the inner walls are made from plastic.

13. The dispenser according to claim 1, wherein each antenna is a coaxial cable.

14. The dispenser according to claim 1, wherein the reader further comprises:
   at least one reader module configured to read the at least one information item stored in the memory of each electronic tag and to send a signal comprising the at least one information item to a controller outside the dispenser; and
   a multiplexer connecting the antennas to the reader module.

15. The dispenser according to claim 1, wherein the reader is able to emit or receive a signal having a frequency of between 13.540MHz and 13.567 MHz.

16. The dispenser according to claim 1, wherein the dispenser has a volume smaller than 0.1 m$^3$.

17. An assembly for controlling at least one container comprising a medical product, the at least one container being provided with an electronic tag comprising a memory storing at least one information item specific to said medical product, the dispenser comprising at least one dispenser according to claim 1.

18. A control facility for at least one container comprising a medical product, the at least one container being provided with an electronic tag comprising a memory storing at least one information item specific to said medical product, the facility including the assembly of claim 17.

19. A control method for at least one container comprising a medical product, the control method being implemented using a dispenser including a reader, the at least one container being provided with an electronic tag comprising a memory storing at least one information item specific to said medical product, the dispenser comprising a plurality of inner walls delimiting a storage volume, the plurality of inner walls comprising side walls and a lower wall on which the containers or the parcel comprising the containers are intended to rest, the side walls delimiting a single access opening to the storage volume, the reader comprising a plurality of loop-shaped antennas, each side wall including a support which is able to house at least part of one of the antennas,
   wherein the plurality of walls comprises outer walls, each outer wall being made from an electrically conductive material having an electrical conductivity greater than or equal to 0.3 MS.cm$^{-1}$, the outer walls delimiting an inner volume, the storage volume being arranged in the inner volume,
   the dispenser being able to receive the at least one container or a parcel comprising the at least one container in the storage volume,
   the method comprising at least the reading by the reader of the at least one information item stored in the memory of each electronic tag.

* * * * *